(12) United States Patent
Mazor et al.

(10) Patent No.: US 10,568,783 B2
(45) Date of Patent: *Feb. 25, 2020

(54) APPARATUS FOR HANDLING SOILED ARTICLES

(71) Applicants: Meital Mazor, Carlsbad, CA (US); Rabih Nassif, Santa Ana, CA (US)

(72) Inventors: Meital Mazor, Carlsbad, CA (US); Rabih Nassif, Santa Ana, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 15/980,697

(22) Filed: May 15, 2018

(65) Prior Publication Data

US 2018/0256418 A1 Sep. 13, 2018

Related U.S. Application Data

(63) Continuation of application No. 15/162,615, filed on May 24, 2016, now Pat. No. 9,993,373, which is a continuation of application No. 14/504,362, filed on Oct. 1, 2014, now Pat. No. 9,370,452.

(51) Int. Cl.
| | |
|---|---|
| *A61F 13/551* | (2006.01) |
| *B65F 1/00* | (2006.01) |
| *B65D 21/08* | (2006.01) |
| *B65D 33/18* | (2006.01) |
| *B65D 81/26* | (2006.01) |

(52) U.S. Cl.
CPC .......... *A61F 13/5518* (2013.01); *B65D 21/08* (2013.01); *B65D 33/18* (2013.01); *B65D 81/264* (2013.01); *B65F 1/00* (2013.01); *A61F 2013/55195* (2013.01); *B65F 2210/1023* (2013.01); *B65F 2210/129* (2013.01); *B65F 2240/164* (2013.01)

(58) Field of Classification Search
USPC ............ 206/438, 440, 812, 823; 604/385.02, 604/385.13; 294/1.3, 1.4
See application file for complete search history.

(56) References Cited

U.S. PATENT DOCUMENTS

| | | | | | |
|---|---|---|---|---|---|
| 2,430,155 | A | * | 11/1947 | Buttery | ............... B65B 67/1205 141/390 |
| 3,804,093 | A | * | 4/1974 | Fell | .......................... A61F 5/448 604/355 |
| 4,349,104 | A | * | 9/1982 | Hayes | .................... B65D 33/00 206/205 |
| 4,553,969 | A | * | 11/1985 | Taylor | ..................... A61F 5/441 604/355 |

(Continued)

*Primary Examiner* — Jacob K Ackun
(74) *Attorney, Agent, or Firm* — Anatoly S. Weiser, Esq.; IPLCounsel

(57) ABSTRACT

A tampon disposal device includes a tubular stiffener, and a membrane conforming to the stiffener with an opening on one end and an enclosure opposite the opening. The membrane is folded inside the stiffener into a first layer attached to the stiffener; and second and third layers that form a lip surrounding the stiffener near a stiffener rim. The second layer folds over the rim, reversing direction to become the third layer lip portion. The third layer continues inside the stiffener. A weak adhesive attaches the lip to the outside stiffener. Another adhesive attaches the first layer to the second layer inside the stiffener. When a hand grasps a tampon siring with the membrane and pulls on the string, the first adhesive allows the lip to separate and be pulled into the stiffener together with the tampon. Pushing inwardly on the stiffener seals the tampon inside the membrane.

17 Claims, 5 Drawing Sheets

(56) References Cited

U.S. PATENT DOCUMENTS

| | | | | | |
|---|---|---|---|---|---|
| 4,648,867 | A * | 3/1987 | Conner | A61F 13/26 | 604/14 |
| 4,838,327 | A * | 6/1989 | Ambler | A61F 15/003 | 141/114 |
| 5,193,684 | A * | 3/1993 | McDonald | A61F 13/34 | 206/438 |
| 5,287,960 | A * | 2/1994 | Kalb | A61F 15/001 | 206/210 |
| 6,131,736 | A * | 10/2000 | Farris | A61F 13/15211 | 206/440 |
| 6,733,482 | B1 * | 5/2004 | Coles | A61F 5/451 | 604/355 |
| 6,939,333 | B1 * | 9/2005 | Franklin, Jr. | A61F 13/47227 | 604/11 |
| 7,056,310 | B2 * | 6/2006 | Tanaka | A61F 5/451 | 604/327 |
| 7,238,173 | B1 * | 7/2007 | Dobbs | A61F 13/5518 | 206/438 |
| 7,422,106 | B1 * | 9/2008 | Kendra | A61F 15/003 | 206/204 |
| 7,722,099 | B2 * | 5/2010 | Bland | B65B 67/00 | 294/1.3 |
| 7,988,681 | B2 * | 8/2011 | McGarity | A61J 19/00 | 220/9.1 |
| 2003/0127343 | A1 * | 7/2003 | Hummel | B65D 75/04 | 206/204 |
| 2005/0098466 | A1 * | 5/2005 | Thomas | A61F 13/5518 | 206/440 |
| 2006/0106357 | A1 * | 5/2006 | McLean | A61F 13/551 | 604/385.02 |
| 2006/0212015 | A1 * | 9/2006 | Peele | A61F 13/5518 | 604/385.13 |
| 2007/0055213 | A1 * | 3/2007 | Erekson | A61F 13/15252 | 604/385.13 |
| 2007/0083179 | A1 * | 4/2007 | Fuentes | A61F 15/003 | 604/385.02 |
| 2008/0041017 | A1 * | 2/2008 | Klippen | A61F 13/55115 | 53/427 |
| 2009/0026101 | A1 * | 1/2009 | Hicks | B65F 1/0006 | 206/438 |
| 2011/0036737 | A1 * | 2/2011 | Luzzatto | A61F 13/55175 | 206/440 |
| 2013/0110062 | A1 * | 5/2013 | Glenn | A61F 13/84 | 604/359 |
| 2014/0276522 | A1 * | 9/2014 | Thompson | A61F 13/5518 | 604/385.02 |
| 2015/0257949 | A1 * | 9/2015 | Thompson | A61F 13/5518 | 383/105 |
| 2017/0224557 | A1 * | 8/2017 | Montalvo | A61F 13/55185 | |
| 2017/0319408 | A1 * | 11/2017 | Jackson | A61F 13/84 | |

* cited by examiner

APPARATUS FOR HANDLING SOILED ARTICLES

CROSS-REFERENCE TO RELATED APPLICATIONS

This application is a continuation of and claims priority to U.S. patent application Ser. No. 15/162,615, entitled APPARATUS FOR HANDLING SOILED ARTICLES, filed May 24, 2016, now allowed; which is a continuation of U.S. patent application Ser. No. 14/504,362, entitled APPARATUS FOR HANDLING SOILED ARTICLES, filed Oct. 1, 2014, now U.S. Pat. No. 9,370,452. Each of the patent documents identified above is hereby incorporated by reference in its entirety as if fully set forth herein, including Specification, Figures, Claims, and all other matter.

FIELD OF THE INVENTION

This document relates generally to the field of removal and disposal of used personal hygiene and similar soiled or contaminated articles. In particular, this document relates to removal and disposal of soiled tampons.

BACKGROUND

Sanitary tampons serve a well-known function. Their disposal presents problems that have become more common with increased personal mobility and activity.

Soiled tampon removal typically requires that the user hold the string attached to the tampon for this purpose, and pull on the string. It is desirable to remove the tampon without the tampon's contacting the user's hand or clothes, and to do so quickly and with minimal inconvenience.

Tampon disposal presents additional challenges. Throwing the tampon into a garbage cars may expose sanitation workers to the bodily fluids of the tampon's user, and cause unpleasant smells; toilet flushing may clog the plumbing. Moreover, in some situations neither a garbage can nor a bathroom may be readily available to the user, necessitating storing the soiled tampon until a proper disposal means presents itself. It is desirable to provide an improved device for storing a soiled tampon in a sanitary manner, without unnecessary smell or contamination.

SUMMARY

A need exists in the art for devices that facilitate removal of soiled hygienic articles, such as tampons. A need also exists in the art for devices that facilitate storage and disposal of soiled hygienic articles, such as tampons. Embodiments of the present invention are directed to apparatuses and articles of manufacture that may satisfy one or more of these and possibly other needs.

In an embodiment, a device for handling soiled articles includes a stiffener. The stiffener has an enclosed wall with an inner stiffener surface and an outer stiffener surface, the wall forming a first rim and a second rim. The device also includes a membrane made of a membrane material. The membrane has a first part configured to conform to the inner stiffener surface and including portions defining a membrane opening, and a second part enclosing the membrane opposite the membrane opening. The membrane is folded inside the stiffener into a plurality of layers, including a first layer that is adhesively attached to at least one of the inner stiffener surface and the outer stiffener surface, a second layer, and a third layer. The second layer includes a second layer lip portion and the third layer including a third layer lip portion, the second layer lip portion and the third layer lip portion forming a lip circumferentially surrounding the outer stiffener surface proximate the first rim, the second layer folding over the first rim to form the second layer lip portion and reversing direction to become the third layer lip portion of the third layer, the third layer continuing inside the stiffener. The device also includes a first weak adhesive attaching the second layer lip portion to at least one of the outside stiffener surface and the first layer, and a second adhesive attaching the first layer to the second layer inside the stiffener, wherein the second adhesive extends circumferentially inside the stiffener. The device is such that, when the membrane is pulled (e.g., by a hand) in a general direction from the first rim to the second rim, the first weak adhesive allows the second layer lip portion to separate from the third layer lip portion so that the lip is pulled into the stiffener, and the second adhesive allows the second layer to separate from the first layer with at least part of the second adhesive remaining disposed circumferentially on the first layer, so that pushing inwardly on the stiffener near said at least part of the second, adhesive seals the contents (such as a soiled tampon) inside the membrane.

In aspects, the first layer folds over the first rim and Is adhesively attached to the outer stiffener surface; and the first weak adhesive includes one or more tabs, does not extend circumferentially around the stiffener, and the one or more tabs are disposed between the second layer lip portion and the first layer attached to the outer stiffener surface.

In aspects, the second part of the membrane is shaped as a dome or another shape that facilitates grasping the tampon string.

In aspects, the membrane and the stiffener are made as one component of the same material, which material is nylon, polyethylene, polyvinyl chloride, latex, silicone, impregnated fabric, impregnated paper, polyester, rubber, or any other plastic. The stiffener is thicker than the flexible membrane.

In aspects, the stiffener is creased and flattened into a flattened state before use.

In aspects, the stiffener further includes portions defining indents for receiving inward pressure from fingers to expand the stiffener from the flattened state.

In aspects, in expanded state of the stiffener, the second rim defines a substantially round opening of between about three inches and about six inches in diameter; and the stiffener is between about two inches and about six inches in height.

In aspects, the stiffener further includes means for expanding the stiffener from the flattened state.

In aspects, the membrane is non-transparent.

In aspects, at least some portion of the membrane is textured to facilitate grasping a tampon string by hand through the membrane.

In aspects, the membrane material is hypoallergenic.

In aspects, the second, rim and the first rim have substantially same dimensions, so that the stiffener in expanded state is circularly-cylindrical with a constant or substantially constant diameter.

In aspects, the stiffener is conical or tapered to facilitate access to membrane.

In aspects, the device further includes an absorbent material attached to the membrane to absorb the contents.

In aspects, the device further includes means for reducing malodor from the content.

In aspects, the device further includes means for absorbing the contents and reducing malodor from the contents.

In aspects, hand-pushing inwardly on the stiffener near said at least part of the second adhesive causes the device to seal in a liquid-tight manner the contents inside the membrane.

In aspects, the first layer is adhesively attached to the inner stiffener surface and to the outer stiffener surface.

In aspects, the second adhesive has stronger adhesion to the first layer than to the second layer.

In aspects, an area of the first layer that is designed to come into contact with the second adhesive is prepared (e.g., by roughening it) to increase adhesion between the first layer and the second adhesive, and an area of the second layer that is designed to come into contact with the second adhesive is not prepared to increase adhesion between the second layer and the second adhesive.

These and other features and aspects of the present invention will be better understood with reference to the following description, drawings, and appended claims.

DETAILED DESCRIPTION

Figure 1:
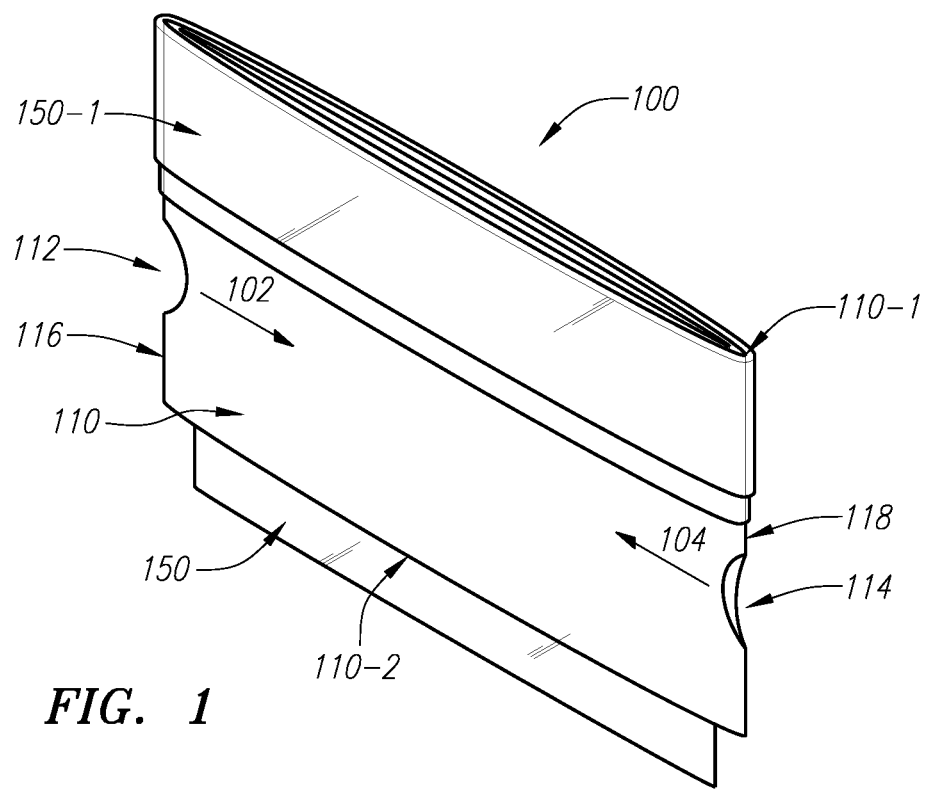
FIG. 1 is a perspective view of an exemplary removal and disposal device in a folded state.

In this document, the words "embodiment," "variant," and "example" refer to particular apparatus, process, or article of manufacture, and not necessarily to the same apparatus, process, or article of manufacture. Thus, "one embodiment" (or a similar expression) used in one place or context can refer to a particular apparatus, process, or article of manufacture; the same or a similar expression in a different place can refer to a different apparatus, process, or article of manufacture. The expression "alternative embodiment" and similar expressions and phrases are used to indicate one of a number of different possible embodiments. The number of possible embodiments is not necessarily limited to two or any other quantity. Characterization of an item as "exemplary" and the use of similar characterizations mean that the item is used as an example. Such characterization of an embodiment does not necessarily mean that the embodiment is a preferred embodiment; the embodiment may but need not be a currently-preferred embodiment. All embodiments are described for illustration purposes and are not necessarily strictly limiting.

Other and further definitions and clarifications of definitions may be found throughout this document.

Reference will now be made in detail to several embodiments that are illustrated in the accompanying drawings. Same reference numerals are used in the drawings and the description to refer to the same apparatus elements and method steps. The drawings are in simplified form, not to scale, and omit apparatus and articles of manufacture elements and method steps that can be added to the described apparatuses, articles of manufacture, and methods, while possibly including certain optional elements and steps. For purposes of convenience and clarity only, directional terms, such as top, bottom, left, right, up, down, over, above, below, beneath, rear, and front, may be used with respect to the accompanying drawings. These and similar directional terms should not be construed to limit the scope of the invention in any manner. Note also that the words such as "connect," "couple," "attach," and similar terms with their inflections do not necessarily denote direct and immediate connections/attachments; they include within their meaning direct/immediate connections, couplings, and attachments, as well as connections, couplings, attachments using intermediate elements or devices.

Figure 2:
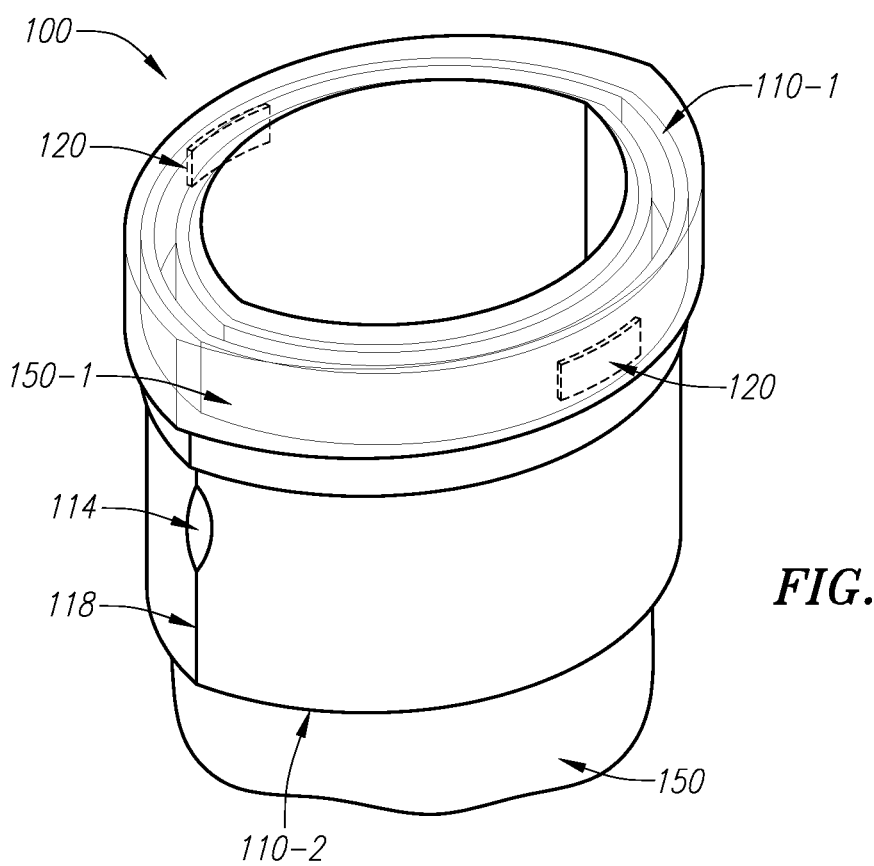
FIG. 2 is a perspective view of the exemplary removal and disposal device in an expanded state.

Referring more particularly to the drawings, FIG. 1 is a perspective view of an exemplary tampon removal and disposal device 100, in a folded state. Keeping the device 100 in the folded state reduces the volume of the device, making it less expensive to ship and store, and also facilitates carrying the device, for example, in a hand bag. Additionally, the device is less prone to damage in the folded state. FIG. 2 is a perspective view of the removal and disposal device 100 in expanded state. The device 100 may be expanded, for example, by applying inward pressure on indents 112 and 114 located on creases 116 and 118 of a stiffener 110. The pressure may be applied, for example, by fingers along the directions indicated by arrows 102 (for the indent 112) and 104 (for the indent 114). In embodiments, each indent is in the shape of a circular or somewhat oblong arc, for example, between about 90° and 180°, and about ⅛ to about ⅜ of an inch (about 3 to about 9.5 mm) deep. In embodiments, the indents 112 are replaced by rubberized grip surfaces, which may be over-molded on the stiffener 110, Each indent (or another means for facilitating expanding the stiffener, such as the rubberized grip surfaces) may be of a form and depth to accommodate a thumb and index finger of an average woman. In some embodiments, the indents may be entirely absent, or replaced by visible markings, texturing, slight protrusions, and/or other features to indicate and/or facilitate expansion of the device 100 by applying pressure with the users fingers. The markings may include arrows indicating the direction for applying pressure to expand the device 100, for example, arrows substantially in the shape and location of the arrows 102/104.

The stiffener 110 may be a wall enclosing a volume between two parallel planes. In the specific embodiment illustrated in the Figures, the stiffener 110 is shown as a cylindrical (in the conventional sense, i.e., a circularly-cylindrical with constant diameter) component which, in the expanded state, has the diameter of its upper rim 110-1 equal or substantially equal to the diameter of its lower rim 110-2. In other embodiments, however, the stiffener 110 may be of a somewhat tapered in shape, with the two diameters being somewhat or even substantially different. In some embodiments, the stiffener 110 has an elliptical cross-section, with the rims 110-1 and 110-2 being of substantially equal or unequal sizes. Other shapes are not necessarily excluded.

As will become clear from the description below, the size of the stiffener should allow a user to insert a hand (or at least several fingers) through the lower rim 110-2, to grasp a tampon string through a membrane 150 and pull the tampon out. In embodiments, the stiffener 110 is cylindrical or substantially cylindrical, with a diameter of between about three and about six Inches (about 76 to 152 mm), with the height of between about two and about six inches (about 51 to about 152 mm). Here, as elsewhere, we merely provide specific examples, and other dimensions and parameters are included within the scope of the present description.

The stiffener 110 may be made of carton, plastic, fabric (which may be impregnated), various paper products, latex and other plastics, robber, other materials, and combinations of the above-listed and other materials. In embodiments, the material of the stiffener 110 is hypoallergenic.

In FIG. 1, reference numeral 150 indicates the membrane 150 that is folded inside the stiffener 110 and attached to the inside of the stiffener 110, with a portion of the membrane 150 shown as protruding slightly below the stiffener 110. The portion of the membrane 150 protruding below the stiffener 110 is also shown in FIG. 2. As can be seen, it may be loose and baggy-shaped; it may also be folded with its inside surfaces touching each other, to reduce storage space, and it may also be folded so as not to protrude below the lower rim 110-2 of the stiffener 110 until the user is ready to use the device 100. The membrane 150 also has an upper lip 150-1, which is folded over the upper portion of the stiffener 100. In embodiments, absorbent materials (i.e., cloth, fleece) and/or odor suppressants (e.g., perfumes, deodorants) may be placed inside the membrane 150, to reduce malodors from soiled tampons after use and to reduce the chances of spillage from the device during removal and disposal. The membrane is flexible, to allow operation of the device 100 by hand to remove and seal a tampon, as is described throughout this document.

The membrane 150 may be made, for example, from various plastic materials, such as nylon, polyethylene, polyvinyl chloride (pvc), latex, silicone, impregnated fabric, impregnated paper, rubber, and polyester. In embodiments, the membrane is between about 0.4 and about 2.0 mils (about 0.01 mm to about 0.05 mm) thick; in more limited embodiments, the membrane is between 0.75 to 1.5 mil (about 0.02 to about 0.04 mm) thick. Some embodiments use membranes thinner than 0.04 mil, and still other embodiments use membranes thicker than 2.0 mil. In embodiments, the thickness of the membrane 150 varies from area to area. Various plasticizers may be added to the material of the membrane to achieve sufficient plasticity in typical use, that is, to allow easy insertion of the hand into the membrane, tampon removal, and subsequent storage/disposal of the tampon, as will be discussed below. The amount of plasticizer may be increased as the thickness of the membrane increases.

Although the membrane 150 may be transparent, there is a certain benefit in reducing the transparency of the membrane, to obscure its contents after use. To this end, color dyes and other concentrates may be added to the material of the membrane 150.

Because the membrane may come into contact not only with the user's hand, but also with outside portions of a bodily orifice, the membrane's material and coloring may be hypoallergenic.

Some texturing may be applied to the portions of the membrane that are designed to come into contact with the user's hand and/or with the string attached to the tampon, to facilitate the user's grasping of and pulling on the string. In embodiments, the side of the membrane 150 that comes into contact with the string includes both a textured portion for facilitating grasping of the string, and a relatively smooth portion (smoother that the textured portion) to avoid unnecessary irritation where the membrane 150 may come into contact with the outside of the bodily orifice. In embodiments, the portion that may come into contact with the bodily orifice may be covered with absorbent material. In embodiments, substantially all of the portion of the membrane 150 that may come into contact with the bodily orifice may be covered with the absorbent material, which may serve both to absorb the user's bodily effluents (e.g., blood) and to increase the traction between the membrane 150 and the tampon string.

Figure 3:
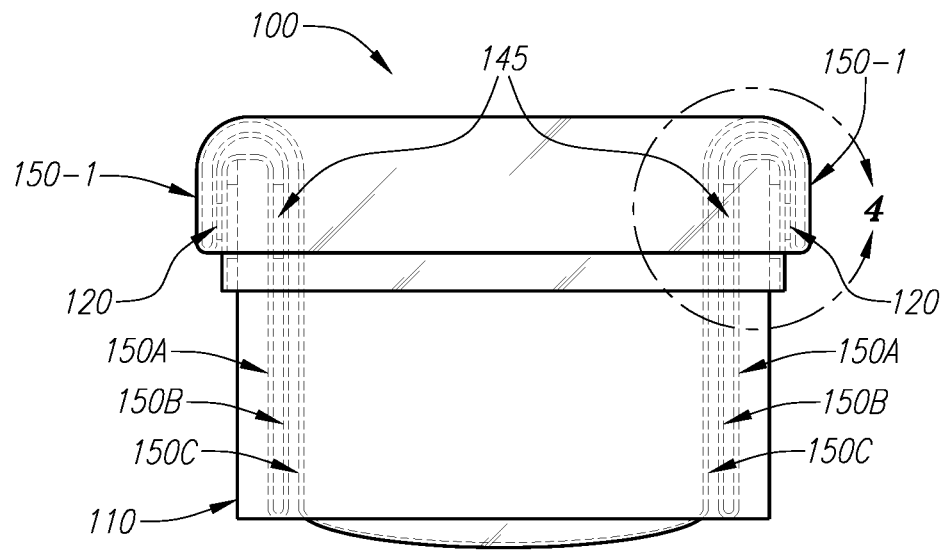
FIG. 3 is a side view of the exemplary removal and disposal device.
Figure 4:
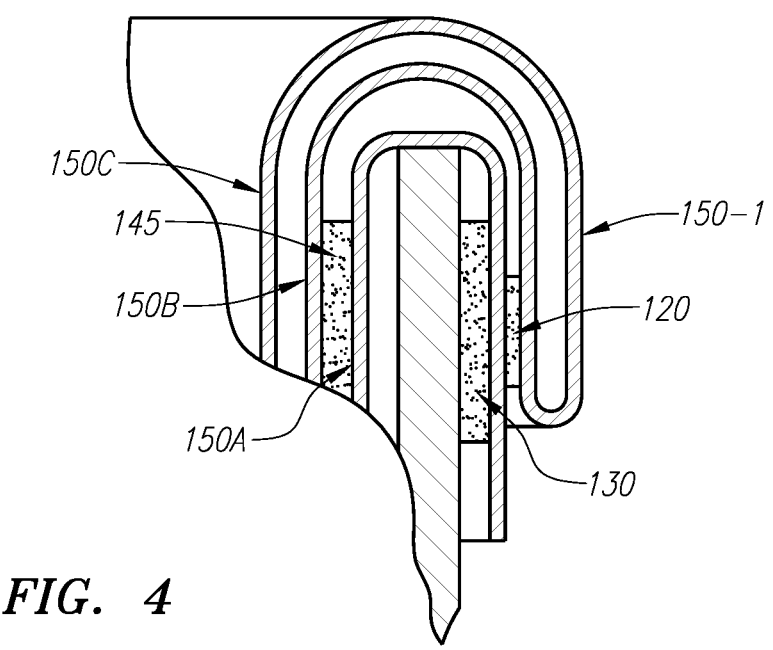
FIG. 4 is a magnified cross-sectional view of a cutaway of the corner of the exemplary removal and disposal device.

FIG. 3 is a side view of the device 100. FIG. 4 is a magnified cross-sectional view of a cutaway "4" of the top right corner (as shown in FIG. 3) of the device 100. Note that in the Figures there are three layers of the membrane 150. The first of these layers is labeled with a reference designator 150A. It is attached (e.g., glued by a strong adhesive layer 130) to the outside of the upper portion of the stiffener 110, then folds over the top rim 110-1 of the stiffener 110 onto the inner wall of the stiffener 110, and follows the inside wall of the stiffener 110 towards the lower portion of the stiffener 110. The layer 150A may be attached to the inside wall of the stiffener 110. In embodiments, the layer 150A begins at the top rim 110-1 rather than at the outside wall of the stiffener 110; in embodiments, the layer 150A begins from the inside wall of the upper portion of the stiffener 110 near the top rim 110-1, or even lower on the inside wall. The adhesive used for attachment of the layer 150A to the stiffener 110 may be strong enough to prevent separation of the layer 150A from the stiffener 110 in normal use and storage, as well as during unfolding of the membrane 150 (described below) and some rough handling of the device 150 when it is carried in a handbag; it may but need not be a "weak" adhesive as that term is defined below.

As the layer 150A approaches the lower portion of the stiffener 150, it reverses direction and continues upward. This is the second layer 150B. Note that the precise point on the vertical axis where the layer 150A reverses direction and turns into the layer 150B may vary, for example, from the bottom rim 110-2 to about half way between the bottom rim 110-2 and the top rim 110-1, or even higher.

The layer 150B folds over the top rim 110-1, and continues downward to form the inside portion of the lip 150-1, The layer 150B then reverses direction, becoming the third layer 150C. This third layer forms the outside portion of the lip 150-1, and folds over the top rim 110-1, continuing down the inside wall of the stiffener 110. In embodiments, the length (vertically as shown on FIG. 3) of the lip 150-1 is between about ⅛ and about 3 inches (about 3 mm to about 76 mm); in more limited embodiments, the length of the lip 150-1 is between about ¼ inch and about one inch (between about 6 mm and about 25 mm).

To keep the lip 150-1 attached to the outside of the stiffener 110, an adhesive may be used between the lip 150-1 (e.g., the layer 150B) and the layer 150A or the outside wall of the top of the stiffener 110. (The latter case is where the layer 150A begins at the top rim 110-1 or on the inside wall of the stiffener 110.) As shown in the Figures, there are two adhesive tabs 120 between the layers 150A/B. Each of the tabs 120 may be rectangular or round and approximately 0.25-0.5 square inches in area, but smaller and larger adhesive tabs of whatever shape are included within the scope of this document; in embodiments, the tabs 120 have various shapes and their number may be greater than two; in embodiments, there is a single adhesive tab, which may be (but does not necessarily have to be) band-like, that is, going around the circumference of the device 100. The adhesive used here may be a "weak" adhesive, designed for non-permanent attachment; it may be similar to the glue used on sticky notes. Functionally, the adhesive and the contact area of the tabs 120 should allow easy separation in manual operation (as will be described below), without tearing of the membrane 150, yet preserve the shape of the lip 150-1 of the membrane 150 while the device 100 is transported and stored during distribution and in retail stores, and then earned by the user.

Another adhesive coating 145 is also located between the layers 150A and 150B, but on the inside of the stiffener 110, and towards the upper end of the stiffener 150. This adhesive coating 145 may be a continuous band that goes around the device 100. It may be designed to provide "weak" adhesion between the membrane layers 150A and 150B, so that these layers can be separated when the bottom portion of the membrane 150 is palled down in operation, as will be described below. The separation should be such that the adhesive coating 145 (or a large portion thereof, such as 50 percent or more) remains on the membrane layer 150A, for seating the device 100 after tampon removal. We will have more to say about the coating 145 below.

As illustrated in the Figures and described in this document, there are three layers of the membrane 150 inside the stiffener 100. In other embodiments, additional layers may be present. This may be useful where the height of the stiffener 110 is relatively short, to provide sufficient room within the membrane to receive the full, length of the tampon.

Figure 5:
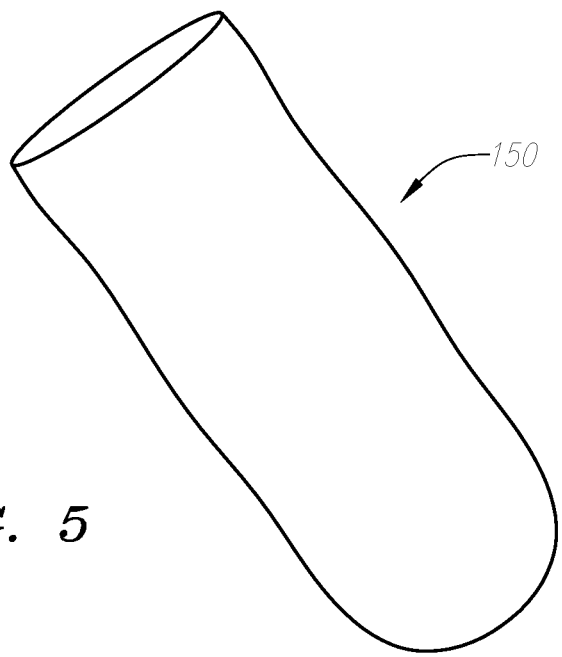
FIG. 5 illustrates an exemplary membrane.
Figure 6:
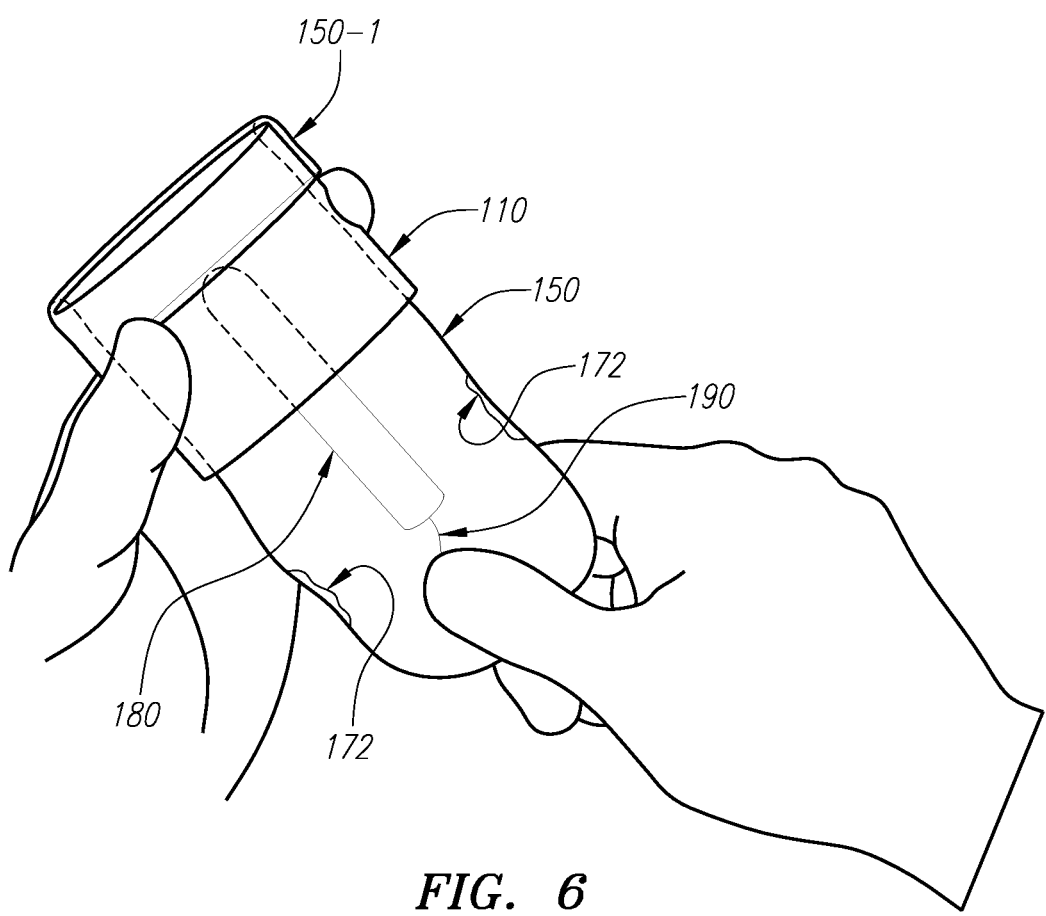
FIGS. 6-11 illustrate selected aspects of steps of an exemplary process of tampon removal and disposal using the exemplary removal and disposal device

FIG. 5 illustrates an embodiment of the membrane 150 by itself. Generally, the membrane 150 may be made as a volume-enclosing surface with an opening (such as the opening 158 in FIG. 5). The membrane 150 has a part substantially conforming to the inner surface of the stiffener 110 (i.e., cylindrical or slightly tapered), with portions at one end defining the opening 158 to correspond to the upper rim 110-1; and an end part 159 at the end opposite the opening 158, which end part 159 may be substantially dome-like (which means shaped as a half of a sphere or the smaller part of a sphere cut off by a plane) and enclose the end that is opposite the opening 158. More generally with respect to the end part 159, it may have a shape that facilitates accessing and grasping a string 190 of a tampon 180, such as trapezoidal shape, conical shape, flatted-square shape, as well as other shapes.

As shown in FIG. 5, the membrane 150 is substantially cylindrical; but as has been noted, the membrane 150 should conform to the stiffener 110 and therefore for a slightly tapered stiffener 110, the membrane 150 would also be slightly tapered.

Figure 7:
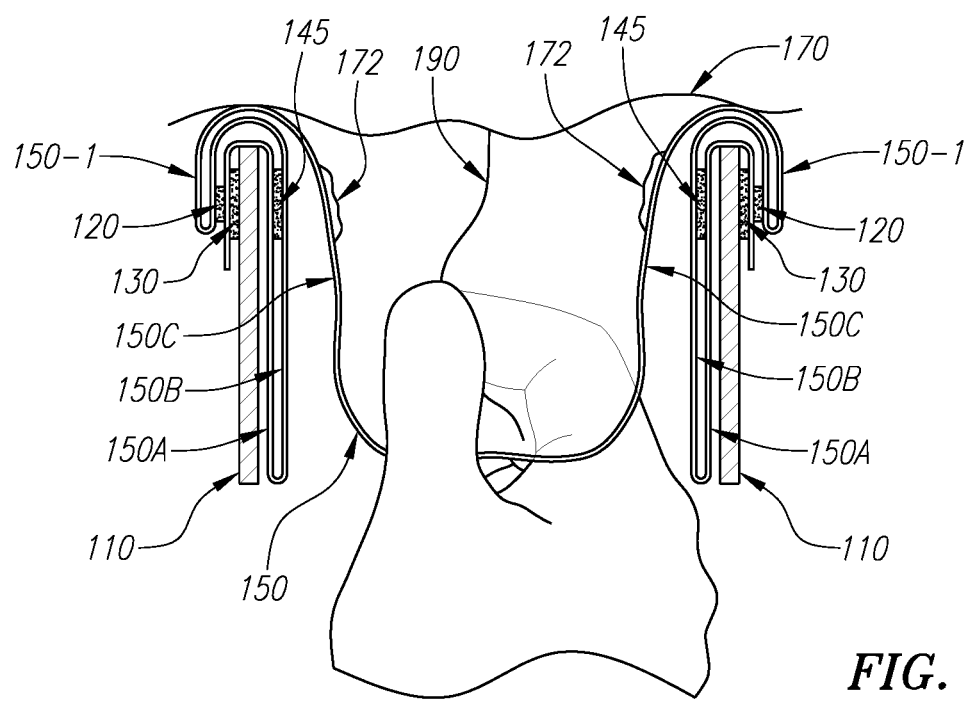

FIGS. 6-11 illustrate selected aspects of the steps of the process of tampon removal and disposal. In FIG. 7, the user brings the top portion of the lip 150-1 into contact with the user's body 170 (particularly the portions of the user's body 170 defining the bodily orifice from which the tampon is removed), and extends the user's fingers up through the bottom opening of the device 100 (defined by the bottom rim 110-2), pushing up and around the membrane 150, so that a string 190 of a tampon 180 is within grasping range of the user's fingers. As the FIG. 7 shows, the user grasps the string 190 not directly, but with the membrane 150. The membrane 150 thus insulates the user's fingers from the soiled tampon 180 and the string 190, as well as from the portions of the user's body proximate the bodily orifice from which the tampon is being removed. A portion of the membrane 150 may touch the user's body 170, or otherwise receive some bodily effluents from the bodily orifice, resulting on the transfer of some soiling material 172 onto the inner portions of the membrane 150.

Figure 8:
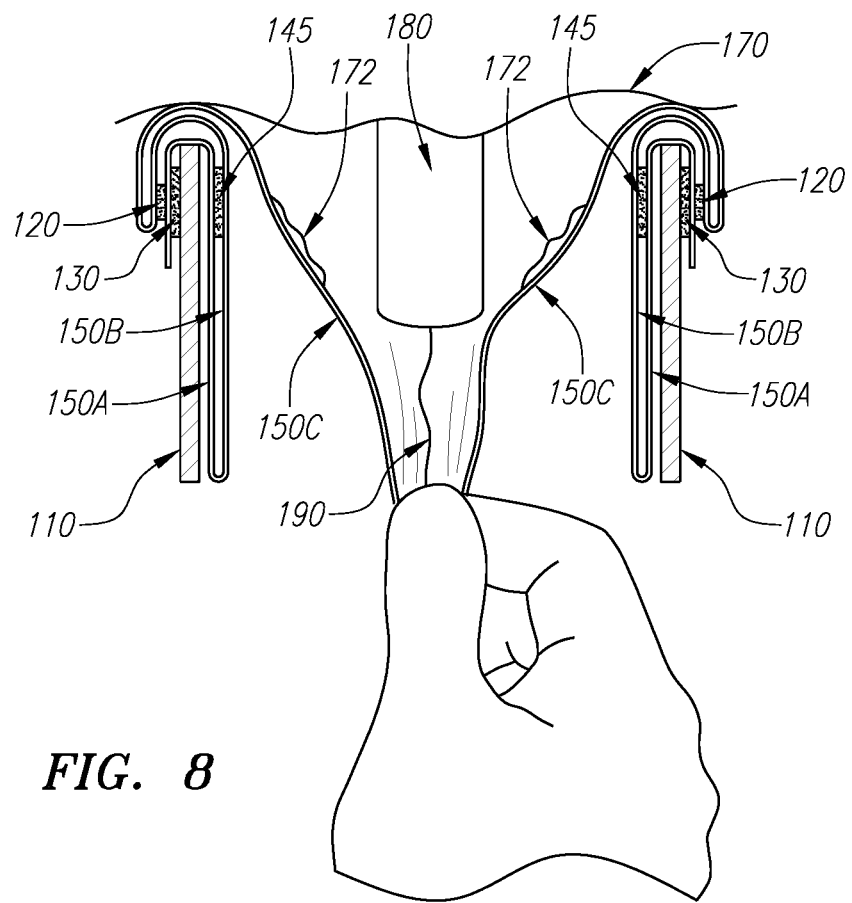
Figure 9:
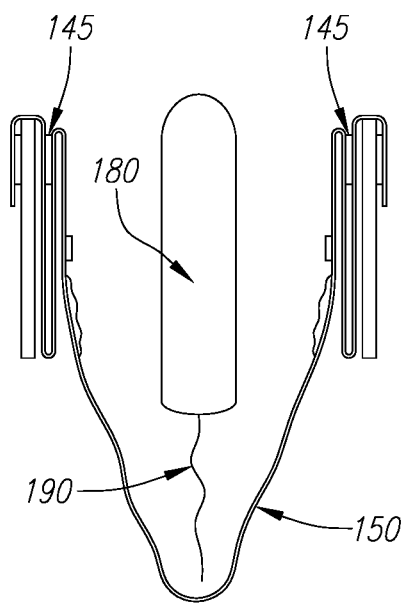
Figure 10:
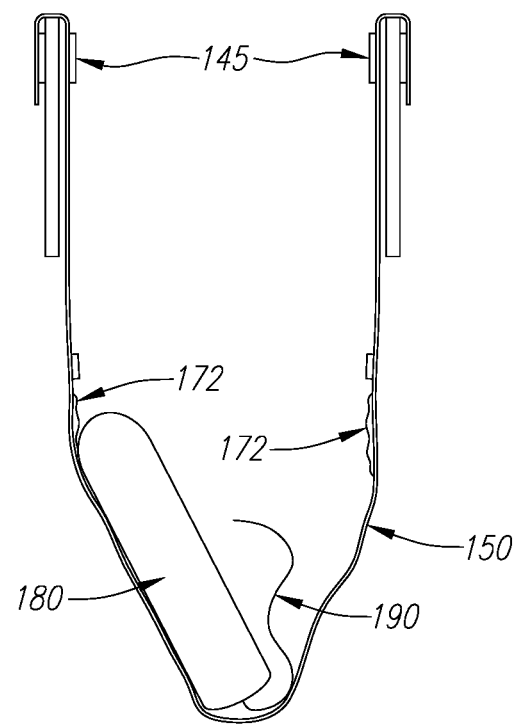

The user then pulls down on the string to remove the tampon from the bodily orifice. FIG. 8 shows the tampon approximately half-way removed from the body. The user continues to pull on the string 190 through the lower central portion of the membrane 150, which action overcomes the adhesion of the tabs 120, releasing the membrane layer 150B from the membrane layer 150A at the lip 150-1. The lip 150-1 then unfolds from the user's pull on the membrane 150, and the membrane extends farther downward, as is illustrated in the FIGS. 6 and 9 (FIG. 9 does not show the user's hand). Further pulling on the lower portion of the membrane 150 overcomes adhesion of the adhesive coating 145, allowing the layers 150A/B/C on the inside of the stiffener 110 to unfold, and extends the membrane 150 still farther down, as is illustrated in FIG. 10. The soiling material 172 travels down with the membrane 150, inside the device 100.

Figure 11:
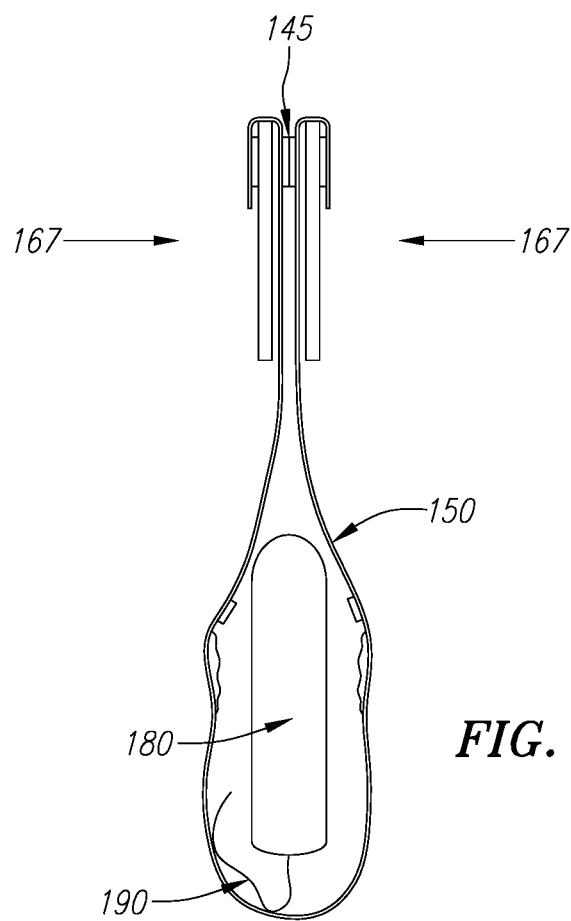

Once the layers 150A/B/C have unfolded, the user lets go of the string 190 and the tampon 180 drops to the bottom of the membrane 150, as is also shown in the FIG. 10. Note that the adhesive coating 145 (or a large portion thereof) remains on the inside of membrane 150A in the form of a complete circumference, and it is supported by the inside wall of the stiffener 110. The user then applies pressure on the outside walls of the stiffener 110 in the direction of the arrows 167 (FIGS. 10 and 11), to close the top of the stiffener 110 by bringing its walls together. The user may apply the pressure between the creases 116/118, to cause the stiffener 110 to fold along these creases. The user continues to apply the pressure to bond the opposite sides of the coating 145 to each other, sealing the tampon 180 and the soiling 172 (if any) within the device 100, as is illustrated in FIG. 11.

As has already been mentioned, the coating 145 may be designed to provide a weaker adhesion to layer 150B than layer 150A such that adhesive coating will stay on layer 150A. This can be achieved by selective surface preparation of adhesion areas of layers 150A and 150B or by preparation of adhesive 145 to have stronger adhesion force on the side of layer 150A than the side of layer 150B. Because the coating 145 extends around the inside of device 100, it may also provide a sufficiently strong adhesive-to-adhesive seal between the opposite sides of the stiffener 110, after the user applies the pressure for sealing the device 100. The seal is preferably liquid-tight.

In embodiments, the stiffener and the membrane of the device are integrated into one component. The single component may be made of the same material, e.g., thicker plastic for the stiffener, thinner plastic for the membrane. The material may thus be flexible at the thickness of the membrane, but stiller at the greater thickness of the stiffener.

The device 100 is particularly useful for removing and disposing tampons and similar articles of female hygiene, but may also be used for removal and disposal of soiled articles from other bodily orifices such as anal orifices, open wounds, and surgical incisions. The device 100 device may be used and/or dispensed in or near bathrooms at various public venues, such as hotels, stadiums, schools, universities, office buildings, and many others.

This document describes in considerable detail the inventive apparatus for handling and disposal of soiled articles removed from a bodily orifice. This was done for illustration purposes. Neither the specific embodiments of the invention as a whole, nor those of its features limit the general principles underlying the invention. The specific features described herein may be used, in some embodiments, but not in others, without departure from the spirit and scope of the invention as set forth herein. Various physical arrangements of components and various step sequences also fall within the intended scope of the invention. Many additional modifications are intended in the foregoing disclosure and it will be appreciated by those of ordinary skill in the art that in some instances some features of the invention will be employed in the absence of a corresponding use of other features. The illustrative examples therefore do not necessarily define the metes and bounds of the invention or inventions and the legal protection afforded the invention(s), which function is may be carried out by the claims and their equivalents.

What is claimed is:

1. A personal hygiene device, comprising:
a stiffener comprising an enclosed wall comprising an inner stiffener surface and an outer stiffener surface, the wall forming a first rim and a second rim;
a membrane made of a membrane material, the membrane comprising a first part including portions defining a membrane opening, and a second part enclosing the membrane opposite the membrane opening, wherein the membrane is folded inside the stiffener into a plurality of layers, the plurality of layers comprising a first layer that is adhesively attached to the inner stiffener surface beginning at the first rim and not extending to fold over the first rim onto the outer stiffener surface, a second layer, and a third layer, the second layer including a second layer lip portion and the third layer including a third layer lip portion, the second layer lip portion and the third layer lip portion forming a lip circumferentially surrounding the outer stiffener surface proximate the first rim, the second layer folding over the first rim to form the second layer lip portion and reversing direction to become the third layer lip portion of the third layer, the third layer continuing inside the stiffener;
a first weak adhesive attaching the second layer lip portion to the outside stiffener surface; and
a second adhesive attaching the first layer to the second layer inside the stiffener, wherein the second adhesive extends circumferentially inside the stiffener;
wherein when the membrane is pulled by hand in a general direction from the first rim to the second rim, the first weak adhesive allows the second layer lip portion to separate from the third layer lip portion so that the lip is pulled into the stiffener, and the second adhesive allows the second layer to separate from the first layer with at least part of the second adhesive remaining disposed circumferentially on the first layer, and so that pushing inwardly on the outer stiffener surface near said at least part of the second adhesive forms a seal that seals contents of the membrane inside the membrane.

2. The personal hygiene device as in claim 1, wherein the first weak adhesive comprises one or more tabs, does not extend circumferentially around the stiffener, and the one or more tabs are disposed between the second layer lip portion and the outer stiffener surface.

3. The personal hygiene device as in claim 1, wherein the first weak adhesive is formed as a band-like shape that extends circumferentially around the stiffener and is disposed between the second layer lip portion and the outer stiffener surface.

4. The personal hygiene device as in claim 3, wherein the membrane material is stretchable.

5. The personal hygiene device as in claim 3, wherein:
the membrane is flexible and the membrane material comprises a first material selected from the group consisting of nylon, latex, silicone, impregnated fabric, impregnated paper, polyester, rubber, and plastic; and
the stiffener is made from a second material, the second material comprises a stiffener material selected from the group consisting of carton, nylon, latex, silicone, impregnated fabric, impregnated paper, polyester, rubber, and plastic.

6. The personal hygiene device as in claim 3, wherein:
the membrane and the stiffener are integrated into one component made of same material selected from the group consisting of nylon, latex, silicone, impregnated fabric, impregnated paper, polyester, rubber, and plastic; and the stiffener is thicker than the membrane.

7. The personal hygiene device as in claim 3, wherein the stiffener is creased and flattened into a flattened state to facilitate shipping and carrying.

8. The personal hygiene device as in claim 7, wherein the stiffener further comprises portions defining indents for receiving inward pressure from fingers to expand the stiffener from the flattened state into an expanded state, the portions defining the indents being disposed on creases formed when the stiffener is creased and flattened into the flattened state.

9. The personal hygiene device as in claim 7, wherein the stiffener farther comprises means for expanding the stiffener from the flattened state.

10. The personal hygiene device as in claim 3, wherein the membrane is non-transparent.

11. The personal hygiene device as in claim 3, wherein at least some portion of the membrane is textured to facilitate grasping a tampon string by hand through the membrane.

12. The personal hygiene device as in claim 3, wherein the membrane material is hypoallergenic.

13. The personal hygiene device as in claim 3, wherein the second, rim and the first rim have substantially same dimensions, so that the stiffener in expanded state is circularly-cylindrical with a substantially constant diameter.

14. The personal hygiene device as in claim 3, wherein the stiffener is tapered.

15. The personal hygiene device as in claim 3, further comprising an absorbent and odor-suppressing material attached to the membrane to come into contact with the contents inside the membrane.

16. The personal hygiene device as in claim 3, wherein finger-pushing inwardly on the stiffener near said at least part of the second adhesive seals the contents inside the membrane in a liquid-tight manner.

17. The personal hygiene device as in claim 3, wherein the second adhesive has stronger adhesion to the first layer than to the second layer.

* * * * *